United States Patent [19]

Peterson et al.

[11] Patent Number: 5,874,474
[45] Date of Patent: Feb. 23, 1999

[54] TOPICAL APPLICATION FOR RELIEF OF ADVERSE SKIN CONDITION FOR ANIMALS

[76] Inventors: Thomas E. Peterson, 1143 Rennie, Katy, Tex. 77450; Byron A. Church, 1814 Rosewood La., Sugar Land, Tex. 77479

[21] Appl. No.: 895,806

[22] Filed: Jul. 17, 1997

Related U.S. Application Data

[60] Provisional application No. 60/021,916 Jul. 17, 1996.
[51] Int. Cl.⁶ .......................... A61K 31/19; A61K 31/185
[52] U.S. Cl. .......................... 514/578; 514/557; 514/829; 514/830; 514/831; 514/886; 514/887; 514/944
[58] Field of Search ...................................... 514/557, 578, 514/429, 830, 831, 886, 887, 544

[56] References Cited

U.S. PATENT DOCUMENTS 4,146,649  3/1979  Seigel et al. ............................. 424/361

OTHER PUBLICATIONS

Merck Index No. 8765, "sodium formate", Jan. 1989.

Merck Index No. 7795, "potassium formate", Jan. 1989.

*Primary Examiner*—Keith D. MacMillan
*Attorney, Agent, or Firm*—Pravel, Hewitt & Kimball

[57] ABSTRACT

This invention is a composition and a method for treating animal skin ailments by a topical application of the composition to the animal in which the composition is a liquid or gel having potassium formate, sodium formate, or cesium formate in water in an effective concentration. Typically, the skin ailments treated are those caused by pyotraumatic dermatitis, chronic itching, scratching and chewing, and flea and insect bites in dogs, cats, horses and other animals.

20 Claims, No Drawings

TOPICAL APPLICATION FOR RELIEF OF ADVERSE SKIN CONDITION FOR ANIMALS

SPECIFICATION

1. Crass-Reference to Related Applications

This application claims priority from provisional patent application Ser. No. 60/021,916 filed Jul. 17, 1996.

2. Field of the Invention

This invention relates to a topical application for dogs, cats, horses and other animals and a method of preparing the same, used to treat adverse skin conditions.

Topical applications for animals for the relief of adverse skin conditions are aqueous based lotions, sprays or ointments applied directly to the animals skin. The applications perform several functions such as drying the skin and inhibiting infection.

It is an object of this invention to provide an improved topical application for animals for the relief of common skin ailments particularly those caused by, but not limited to pyotraumatic dermatitis, chronic itching, scratching and chewing, and flea and insect bites.

In accordance with this invention, a topical application for animals consists of water, preferably purified or distilled water, combined with potassium, and/or sodium, and/or cesium formate in any concentration from 0.1% to 99.1% for each product in liquid form or together with a gelling agent to form a gel application. Preferably, the composition of this invention is in a liquid form with a gelling agent to form a gel in which the concentration of potassium formate, sodium formate, or cesium formate is about 40–60% by volume of the composition, and more preferably, is about 50% by volume.

The term "purified" water as used herein and in the claims means water which has impurities and contaminants, i.e., both solids and liquids, removed. It should be understood that "purified" does not require 100% removal of all impurities and contaminants.

This invention is a composition and a method for treating animal skin ailments by the topical application of the composition to the animal in which the composition is a liquid or gel having potassium formate, sodium formate, or cesium formate in water in an effective concentration. Typically, the skin ailments treated are those caused by pyotraumatic dermatitis, chronic itching, scratching and chewing, and flea and insect bites in dogs, cats, horses, and other animals.

One of the advantages of this invention is that it brings about rapid relief and recovery by drying the epidermis and speeding the healing process.

One of the peculiarities of the invention lies in the active ingredient which promotes healing. Many medications currently on the market rely on steroids, antibiotics or vitamin A cream for relief of the skin problem. This invention relies on potassium, and/or sodium, and/or cesium formate to promote healing.

Topical applications are administered directly on the affected area. The duration of treatment depends upon the severity of the dermatitis. Several applications may be necessary for complete healing.

Although this invention has been disclosed and described in its preferred forms with a certain degree of particularity, it is understood that the present disclosure of the preferred forms is only by way of example and numerous changes in the details of operation and in the combination and arrangement of parts may be resorted to without departing from the spirit and scope of the invention as hereinafter claimed.

What is claimed is:

1. A liquid or gel composition, having an effective amount of potassium, and/or sodium, and/or cesium formate for topical application to animals for the relief and therapeutic treatment of animal skin ailments.

2. The liquid or gel in claim 1 comprising water in which potassium, and/or sodium, and/or cesium formate is present in any concentration from 0.1% to 99. 1% by volume, in liquid form or together with a gelling agent to form a gel application.

3. The liquid or gel in claim 1 comprising water in which potassium, and/or sodium, and/or cesium formate is present in a concentration of about 50% by volume, in liquid form or together with a gelling agent to form a gel application.

4. The liquid or gel in claim 1 comprising water in which potassium, and/or sodium, and/or cesium formate is present in a concentration of about 40–60% by volume, in liquid form or together with a gelling agent to form a gel application.

5. The composition of any one of claims 2, 3, or 4, in which the water is purified or distilled.

6. A method for the therapeutic treating of animal skin ailments, comprising topically applying to the epidermis of animals a liquid or gel composition having an effective amount of potassium, and/or sodium, and/or cesium formate for the relief and therapeutic treatment of animal skin ailments.

7. The method of claim 6, wherein the composition comprises water in which potassium, and/or sodium, and/or cesium formate is present in any concentration from 0.1% to 99.1% by volume, either in liquid form or together with a gelling agent to form a gel application.

8. The method of claim 6, wherein the composition comprises water in which potassium, and/or sodium, and/or cesium formate is present in any concentration from 50% by volume, either in liquid form or together with a gelling agent to form a gel application.

9. The method of claim 6, wherein the composition comprises water in which potassium, and/or sodium, and/or cesium formate is present in any concentration from 40–60% by volume, either in liquid form or together with a gelling agent to form a gel application.

10. The method of any one of claims 7, 8, or 9, in which the water is purified or distilled.

11. A liquid or gel composition, consisting essentially of potassium, and/or sodium, and/or cesium formate for topical application to animals for the relief and therapeutic treatment of animal skin ailments.

12. The liquid or gel in claim 11 comprising water in which potassium, and/or sodium, and/or cesium formate is present in any concentration from 0.1% to 99.1% by volume, in liquid form or together with a gelling agent to form a gel application.

13. The liquid or gel in claim 11 comprising water in which potassium, and/or sodium, and/or cesium formate is present in a concentration of about 50% by volume, in liquid form or together with a gelling agent to form a gel application.

14. The liquid or gel in claim 11 comprising water in which potassium, and/or sodium, and/or cesium formate is present in a concentration of about 40–60% by volume, in liquid form or together with a gelling agent to form a gel application.

15. The composition of any of claims 12, 13, or 14, in which the water is purified or distilled.

16. A method for the therapeutic treating of animal skin ailments, comprising topically applying to the epidermis of animals a liquid or gel composition consisting essentially of potassium, and/or sodium, and/or cesium formate for the relief and therapeutic treatment of animal skin ailments.

17. The method of claim 16, wherein the composition comprises water in which potassium, and/or sodium, and/or cesium formate is present in any concentration from 0.1% to 99.1% by volume, either in liquid form or together with a gelling agent to form a gel application.

18. The method of claim 16, wherein the composition comprises water in which potassium, and/or sodium, and/or cesium formate is present in any concentration from 50% by volume. either in liquid form or together with a gelling agent to form a gel application.

19. The method of claim 16, wherein the composition comprises water in which potassium, and/or sodium, and/or cesium formate is present in any concentration from 40–60% by volume, either in liquid form or together with a gelling agent to form a gel application.

20. The method of any one of claims 17, 18 or 19, in which the water is purified or distilled.

* * * * *